United States Patent [19]

Tremblay et al.

[11] Patent Number: 5,188,951
[45] Date of Patent: Feb. 23, 1993

[54] ENZYMATIC SYNTHESIS OF SOLUBLE PHOSPHATIDES FROM PHOSPHOLIPIDS

[75] Inventors: Paul-Alain Tremblay, Hamilton, N.J.; Frank Marziani, Willow Grove, Pa.; John A. F. Tino; Frank G. Pilkiewicz, both of Cranbury, N.J.

[73] Assignee: The Liposome Company, Inc., Princeton, N.J.

[21] Appl. No.: 694,669

[22] Filed: May 1, 1991

Related U.S. Application Data

[63] Continuation-in-part of Ser. No. 513,285, Apr. 17, 1990, abandoned.

[51] Int. Cl.$^5$ .................... C12P 9/00; C12P 13/00; C12N 9/16; C07F 9/02
[52] U.S. Cl. .................... 435/131; 435/196; 435/128; 558/105
[58] Field of Search .................... 435/128, 196, 131; 558/105, 170

[56] References Cited

U.S. PATENT DOCUMENTS

| | | | |
|---|---|---|---|
| 3,652,397 | 3/1972 | Pardun | 195/30 |
| 4,235,792 | 11/1980 | Hsia et al. | 260/403 |
| 4,485,045 | 11/1984 | Regen | 260/403 |
| 4,587,055 | 5/1986 | Regen | 260/413 |
| 4,783,402 | 11/1988 | Kokusho et al. | 435/52 |
| 4,997,761 | 3/1991 | Jett-Tilton | 435/240.2 |

FOREIGN PATENT DOCUMENTS

| | | |
|---|---|---|
| 0399544 | 11/1990 | European Pat. Off. |
| 62-205788 | 9/1987 | Japan |
| 831129 | 5/1981 | U.S.S.R. |
| 88/06443 | 9/1988 | World Int. Prop. O. |
| 89/01524 | 2/1989 | World Int. Prop. O. |

OTHER PUBLICATIONS

Cazes, "High Performance CPC for Downstream Processing of Biomaterials", American Biological Laboratories, Jun. 1989, 17–23.

Juliano, et al., "Selective Toxicity and Enhanced Therapeutic Index of Liposomal Polyene Antibiotics in Systemic Fungal Infections", Annals N.Y. Acad. Sci., 1985, 446:390–402.

Juneja, et al., "Repeated Batch and Continuous Operations for Phosphatidylglycerol Synthesis from Phosphatidylcholine with Immobilized Phospholipase D", Appl. Microbiol. Biotechnol, 1987, 27:146–151.

Juneja, et al. "Comparative Study on Conversion of Phosphatidylcholine to Phosphatidylglycerol by Cabbage Phospholipase D. in Micelle and Emulsion Systems", Enzyme and Microbial Technology, 9, 6, 1987 350–354.

Lopez-Berestein, et al. "Liposomal Amphotericin B for the Treatment of Systemic Fungal Infections in Patients with Cancer: A Preliminary Study", J. Inf. Dis., 1985, 151, 4:704–710.

*Primary Examiner*—Douglas W. Robinson
*Assistant Examiner*—Susan M. Weber
*Attorney, Agent, or Firm*—Allen Bloom; Ilene Janofsky

[57] ABSTRACT

A method of preparing a soluble monovalent salt of a phosphatidyl ester which comprises reacting a phospholipid with a primary alcohol in the presence of an enzyme catalyst in a divalent cationic buffered solution and a water immiscible non-ether solvent that does not inactivate the enzyme, to form a divalent cationic salt of the phosphatidyl ester, and suspending the product in the presence of a stoichiometric amount of a monovalent cationic salt whose anion forms an insoluble salt with the divalent cation. The use of Centrifugal Partition Chromatography facilitates the enzyme reaction. The monovalent salt is preferably an ammonium/sodium mixed salt.

17 Claims, 1 Drawing Sheet

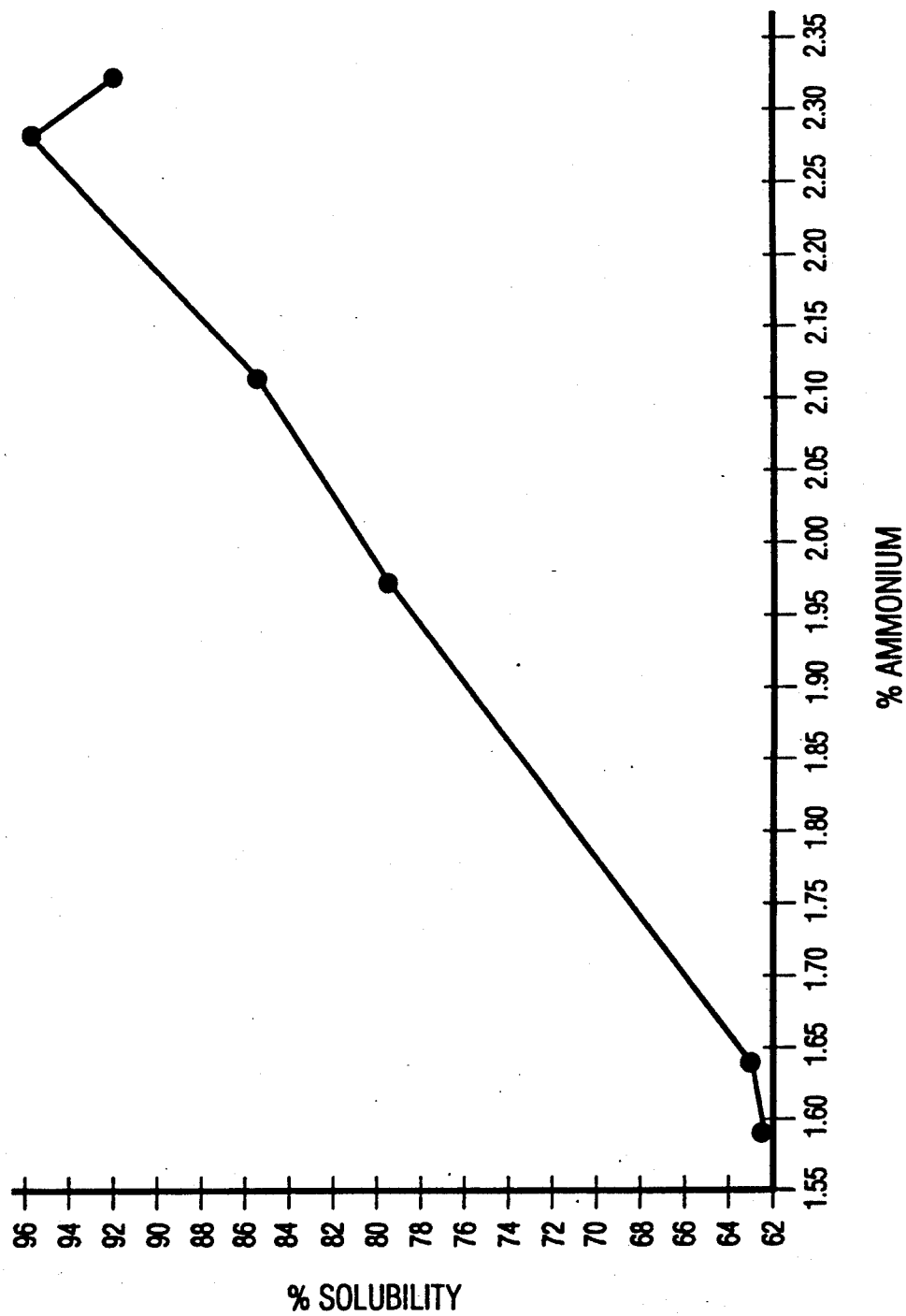

ENZYMATIC SYNTHESIS OF SOLUBLE PHOSPHATIDES FROM PHOSPHOLIPIDS

CORRESPONDING U.S. PATENT APPLICATIONS

This application is a continuation-in-part of copending U.S. application Ser. No. 513,285 filed Apr. 17, 1990, now abandoned.

BACKGROUND OF THE INVENTION

This invention relates to an improved synthesis of soluble phosphatides from phospholipids using phospholipase D enzyme as a catalyst, whereby high yields of high purity soluble phosphatides are obtained.

Phosphatides such as phosphatidyl glycerol are valuable and useful products used for making liposomes and lipid complexes.

Phosphatidyl glycerols and other phosphatides have been made heretofore by mixing an aqueous buffer solution containing calcium acetate, acetic acid and an enzyme, phospholipase D, and glycerol or other primary alcohol, with a phosphatidyl lipid, such as phosphatidyl choline, dissolved in a water immiscible organic solvent. In order to activate the enzyme, either a solvent such as ether has been used, or a surfactant has been added to emulsify the mixture of water insoluble and aqueous solutions.

Dimethyl ether, diethyl ether and other ethers, as has been disclosed by Redemann, PCT Application No. WO 89/01524 published Feb. 23, 1989, have been used to activate the enzyme, but these are known to be hazardous because of their flammability and their peroxide forming properties, which promote the auto-oxidation of the phosphatides. In addition, because of the very low density of ethers as compared to water, good mixing of the mixture of phases requires vigorous shaking, which can be difficult to scale up to commercial quantities.

Surfactants are useful also to activate the enzyme, but they are difficult to remove from the desired product. Thus, elaborate and expensive column chromatography separations are required to obtain a phosphatide of useful purity. Further, the presence of water in relatively large amounts results in hydrolysis and the concurrent production of phosphatidic acid, which reduces the yield of the desired phosphatide product, and which also must be separated from the desired phosphatide.

Further, the enzyme requires an optimum pH range which necessitates the use of buffer solutions. The enzyme also requires a divalent cation such as calcium ion in the reaction mixture which produces the phosphatide as the calcium or other divalent cationic salt, which precipitates out of solution and therefore is difficult to solubilize. If acidification or ion exchange resin and neutralization are used to convert the calcium salts to their more soluble monovalent salts, very rapid hydrolysis occurs, with the concomitant precipitation of products of decomposition such as lysophosphatidyl glycerol or phosphatidyl acid, with the problems enumerated above.

In an attempt to improve the yields of phosphatides such as phosphatidyl glycerol, a process whereby a phosphatidyl lipid is reacted in an organic solvent with phospholipase D fixed on a carrier having hydrophobic groups has been disclosed. The solvent can be diethyl ether or an alkane which can dissolve phosphatidyl lipids such as phosphatidyl choline. The reaction is carried out at a temperature below the boiling point of the organic solvent, such as 15° to 35° C. However, yields of the desired phosphatide are low, on the order of 45%, and use of the ether solvents is inconvenient because they are highly flammable and dangerous solvents.

Thus, a method to produce phosphatides in a safe, simple manner in improved yield and in the form of a water soluble, monovalent, stable salt, has long been sought.

Previously, this transesterification reaction was usually done in a two phase system with ether in order to activate the reaction to a useful rate. However, the reaction was seldom quantitative as significant quantities of phosphatidic acid were also generated. In addition, due to the large difference in densities between the ether and the aqueous phase, large scale reactions gave limited yields due to insufficient mixing. Detergents may be used, but resulted in an increased difficulty in purifying the product.

SUMMARY OF THE INVENTION

In accordance with the invention, a phospholipid such as phosphatidyl choline can be reacted with a primary alcohol in the presence of (i) an enzyme catalyst such as phospholipase D, (ii) a non-ether solvent that is non-destructive and non-denaturing to the enzyme and less flammable than ethers, and (iii) a buffered divalent salt solution, preferably the calcium salt, to form the corresponding phosphatidyl ester as a divalent salt. The insoluble divalent salt is converted to an organic soluble, stable monovalent salt by suspending the divalent salt in an organic solvent, and adding a stoichiometric amount of a solid monovalent salt which simultaneously solubilizes the phosphatide and precipitates the calcium salt of the anion of the added monovalent cation salt. This procedure produces the monovalent salt of the phosphatide without substantial formation of hydrolysis products such as phosphatidyl acid.

It has also been found that for a particular ester salt, dimyristoylphosphatidyl glycerol mixed ammonium/sodium salt, when the ratio of ammonium to sodium ions is a particular ratio by weight, and the amount of the divalent cation present is limited, the solubility and stability of the dimyristoylphosphatidyl glycerol salt is maximized. In order to maximize the stability and solubility of a mixed ammonium/sodium salt of dimyristoylphosphatidyl glycerol in an organic solvent, it has been found that the percent by weight of ammonium ion should be between about 2.0 and about 2.6 percent by weight of the mixed salt, and the percent by weight of sodium ion should be between about 0.3 and about 0.8 percent by weight of the mixed salt. The maximum calcium level should be about 0.1, preferably about 0.05 percent by weight of the mixed salt.

Further, it has been found that Centrifugal Partition Chromatography (CPC) may be used to greatly facilitate the enzyme reaction of phospholipase D with phosphatidyl choline and glycerol or some other alcohol.

BRIEF DESCRIPTION OF THE DRAWING

FIG. 1 is a graph of solubility versus ammonium ion content in methylene chloride for dimyristoylphosphatidyl glycerol mixed salt.

DETAILED DESCRIPTION OF THE INVENTION

The present process is a two step process for forming a monovalent salt of a phosphatidyl ester which comprises:

a) reacting a phospholipid with a primary alcohol in the presence of a suitable enzyme catalyst, such as phospholipase D, and a divalent cationic buffer solution in an aqueous-immiscible solvent having low flammability to form the corresponding insoluble phosphatide of the divalent cationic salt, and b) converting the divalent cationic salt of the phosphatide to its corresponding soluble monovalent salt by suspending it with a stoichiometric amount of a solid monovalent salt whose anion forms an insoluble precipitate with the divalent cation.

Due to their improved solubility and stability, the compounds of this invention, are particularly useful in liposome and lipid complex compositions.

Liposomes are completely closed lipid bilayer membranes containing an entrapped aqueous volume. Liposomes may be unilamellar vesicles (possessing a single bilayer membrane) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "head" orient towards the aqueous phase.

Liposomes comprising dimyristoylphosphatidyl choline (DMPC), dimyristoylphosphatidyl glycerol (DMPG) and cholesterol encapsulating amphotericin B, are useful in the treatment of systemic fungal infections. Juliano et al., Annals N.Y. Acad, Sci., 1985, 446:390–402; Lopez-Berenstein et al., J. Infect, Dis., 1986, 151:704–710.

PCT Publication No. W088/06443, entitled "Low Toxicity Drug-Lipid Systems", Janoff et al., published on Sep. 7, 1988, describes methods of making of high drug:lipid complexes of drug-associated lipids in particulate non-liposomal form, or HDLC's, and liposomes containing a specific ratio of DMPC and DMPG. The phospholipids are solubilized in solvents such as chloroform and methylene chloride.

HDLC's are prepared by first solubilizing a drug, particularly where the drug is a polyethylene antifungal antibiotic such as amphotericin B, in a biocompatible organic solvent, such as dimethylsulfoxide (DMSO) or methanol, and mixing the resultant solution with lipid(s), such as DMPC:DMPG in a 7:3 mole ratio, which have been solubilized in a solvent such as methylene chloride. The solvents are evaporated under reduced pressure, resulting in a thin lipid-drug film. The film is hydrated in an aqueous solution such as saline, PBS, or gylcine buffer, forming HDLC's. Alternatively, the aqueous solution may be added to the solvent-containing drug and lipid phase prior to evaporation of the solvent. As another alternative, the resulting dry lipid-drug film may be resuspended in a solvent, such as methylene chloride and again evaporated under reduced pressure prior to hydrating the film. A dehydration procedure may also be used wherein a dry lipid-drug film is dehydrated to form a flake which is hydrated with aqueous solution. In an alternative method for forming HDLC's, lipid particles containing bioactive agent made by the MLV process are formed and then the particles are subjected to a heating cycle, at about 25° C. to about 60° C.

The phospholipids useful in the present invention are a class of natural and synthetic lipids which contain one or more phosphatidyl groups. They include phosphatidyl choline, phosphatidyl ethanolamine, phosphatidyl serine, phosphatidic acid, dimyristoylphosphatidyl choline and phosphatidyl inositol. Phosphatidyl choline is readily available commercially in high purity and is thus preferred.

The primary alcohol illustrated herein is glycerol, but other primary alcohols such as sulfocholine, ethylene glycol, glycidol, sialic acids, ribose, ethanolamine, glycerolformal and the like can be used. Simple primary alcohols such as methanol, ethanol, propanol and the like must be carefully excluded as they react extremely rapidly to form the corresponding alkyl ester.

Suitable divalent cationic buffers have a pH of about 5.7 and contain a divalent cation such as calcium. The cation should be inactive with respect to the enzyme. For example, the buffer can be a solution of one or more of the following: calcium hydroxide, calcium chloride or calcium acetate with acetic acid or sodium acetate, as an example.

The non-flammable, or low flammable, water immiscible solvent useful in the invention is one that is less flammable than diethyl ether or dimethyl ether; has a flash point of over 0° C., and preferably over 20° C.; and one that will not degrade or denature the enzyme so as to reduce its activity more than about 25% below that of diethyl ether. Suitable solvents for the present process include halogenated solvents such as methylene chloride, chloroform, tetrachloroethylene, trichlorofluoromethane and the like. Aliphatic or aromatic esters, alkanes, ketones or esters having a molecular weight below about 5000 can also be used, such as ethyl acetate, ethyl propionate, ethyl butyrate, methyl acetate, methyl propionate, 3-pentanone, 3-heptanone, 2-octanone, 2-butanone, 2-pentanone, 2-heptanone, 3-octanone and 4-heptanone and the like.

The above reactants are mixed together, as by stirring or shaking to convert the initial phosphatidyl ester, such as phosphatidyl choline, to the divalent cationic salt of the desired product, such as the calcium salt of phosphatidyl glycerol, for example.

Generally low energy mixing such as stirring or vortexing, will be sufficient to obtain at least about 80% of the projected yield of the divalent cationic salt.

Centrifugal Partition Chromatography (CPC), Cazes, J. "High Performance CPC for Downstream Processing of Biomaterials", American Biological Laboratories, June 1989, 17–23 may be used to facilitate the transesterification reaction of the enzyme with the phospholipid and the alcohol. A stationary aqueous phase, consisting of a suitable buffer of about 5.6, such as sodium acetate, is loaded with calcium chloride, a suitable alcohol and the enzyme into the centrifuge. The centrifuge is set into motion and a mobile phase, consisting of an organic nonalcoholic solvent such as ethyl acetate or ethyl butyrate, containing the phospholipid is pumped into the CPC system. The calcium salt of the saturated phosphatidyl glycerol, such as DMPG, precipitates from the eluant. The unreacted soluble phosphatidyl choline is then recirculated to increase the yield. The phosphatidyl glycerol (DMPG) may then be further purified. One skilled in the art would understand conditions to employ for this.

The temperature at which the reaction is run is generally between about 15° C. and 50° C., preferably between about 20° and 37° C., and most preferably about 20° to 30° C.

The divalent cationic salt precipitates and can be readily separated from the enzyme and other by-products of the reaction by filtration, and washing with a water-immiscible organic solvent, such as ethyl acetate followed by methylene chloride, to further purify it.

The divalent cationic salt is converted in the presence of an organic solvent phase, such as methyl alcohol and chloroform, to a soluble monovalent salt by reacting in suspension with about a stoichiometric amount of a monovalent salt whose anion forms a precipitate with the divalent cation. The preferred monovalent cations are ammonium, sodium and potassium as their carbonates, citrates, fluorides, sulfates, phosphates, nitrates, lactates, succinates, formates, oxalates, chlorides ethylene diamine tetraacetates, ethylene bis (oxyethylene nitrilo) tetraacetates and the like, all of which have significant water solubility. The phophatidyl monovalent salts remain in solution and the divalent salt precipitates and can be readily removed by filtration and the like. At least 25% conversion, and generally a 35% conversion or higher, is readily obtained. Because of the volatility of ammonia in ammonium salts, which are desirable because of their high solubility, it is preferred to prepare a mixed ammonium/sodium salt for good solubility and good stability. A preferred molar ion ratio of ammonium to sodium is about 1:1 to about 8:1. A particularly preferred ion ratio of ammonium to sodium is a 4:1 molar ratio.

The ammonium salt of dimyristoylphosphatidyl glycerol is quite soluble in organic solvents such as methylene chloride. The solubility of the ammonium salt of dimyristoylphosphatidyl glycerol in methylene chloride is greater than about 26 mg/ml. However, this salt tends to be unstable. The sodium salt is more stable, but much less soluble; for example, the solubility of sodium salt of dimyristoylphosphatidyl glycerol in methylene chloride is less than about 0.2 mg/ml. Particular proportions of the sodium salt with the ammonium salt will stabilize the mixed salt, but without adversely affecting the solubility below satisfactory levels when the amount of sodium salt is controlled. About 0.3% by weight of the sodium cation confers stability; however, above a maximum amount of about 0.8% by weight of sodium, the solubility of the mixed salt in methylene chloride is decreased.

The amount of residual calcium ion should be limited to below about 0.1, preferably about 0.05 percent by weight of the mixed salt. The calcium salt is insoluble and the presence of excess calcium ion has an adverse effect on the solubility of the mixed salt in relatively non-polar organic solvents.

It is to be noted however that even when the mixed ammonium/sodium salt of dimyristoyphosphatidyl glycerol has a calcium ion content of more than about 0.1 percent or about 0.05 percent by weight and a sodium ion content of more than about 0.8 percent by weight, the solubility of the salt increases markedly when the ammonium ion content is above about 2.0 percent by weight and is very high when the ammonium ion content is about 2.25 to about 2.35 percent by weight (FIG. 1 and Table II).

Generally if the calcium ion content is above about 0.05 percent by weight or if the ammonium ion levels are less than about 2.0 percent by weight, the percent of insolubles of mixed ammonium/sodium salts of dimyristoyphosphatidyl glycerol in methylene chloride increases (see Table III).

Thus, also in accordance with the process of the present invention, after precipitating the calcium salt of dimyristoylphosphatidyl glycerol, washing and filtering, both ammonium carbonate and sodium carbonate is added in an amount to convert the calcium anion to a solid calcium salt, i.e., the carbonate. Preferably monovalent carbonates are not added in excess of the stoichiometric amount needed to precipitate the calcium anion as the calcium carbonate salt. The ammonium/sodium mixed salt of dimyristoylphosphatidyl glycerol is separated from the insoluble calcium salt and can be further purified if desired.

If further purification is desired, chromatographic purification using an ammoniacal silica column can be employed with mixed methanol/chloroform solvents in a known manner.

The process of the invention is carried out in the absence of detergents or other surfactants that generally must later be removed; and it produces a high purity product in high yield, without the concomitant production of phosphatidyl acid or other by-products that reduce the yield of the desired phosphate ester salts, and require purification to remove.

The process of the invention will be further described with reference to the following examples, but the invention is not meant to be limited to the details described therein. All reactions were carried out at about 23° C.

EXAMPLE 1

200 Mg of phosphatidyl choline was emulsified in a solution of 1 ml of concentration of 0.5N sodium acetate buffer having a pH of 5.6, 1 ml of water, 0.2 ml of 1M calcium chloride and 0.2 ml of glycerol.

One mg of phospholipase D in 1 ml of sodium acetate and 1 ml of water were added to the above emulsion and 2 ml of methylene chloride were added and the mixture stirred for 17 hours.

The phosphatidyl glycerol precipitate was filtered, washed with 10 ml of methylene chloride and recovered as the calcium salt in 74% yield.

140 Mg of the calcium salt as obtained above was suspended in 6 ml of ethanol and 3 ml of hexane and a stoichiometric amount of a 1:4 molar mixture of sodium carbonate/ammonium carbonate was added and stirred.

The precipitate of calcium carbonate was removed by filtration.

A yield of 120 mg or 78% of sodium/ammonium phosphatidyl glycerol was obtained.

EXAMPLE 2

100 Grams of dimyristoylphosphatidyl choline were charged to a 5 liter container, 500 ml of water and 500 ml of 0.5N sodium acetate buffer having a pH of 5.6 were added, and 100 ml of M calcium chloride and 100 mg of phospholipase D dissolved in 50 ml of the buffer and 50 ml of water. One liter of ethyl butyrate was added, the container sealed and shaken for 17 hours.

Calcium dimyristoylphosphatidyl glycerol was recovered as a precipitate. The product was filtered on a Buchner funnel, washed with 5 liters of ethyl acetate and given a final 1 liter wash with methylene chloride.

The filter cake was suspended in 1052 ml of methanol, 526 ml of chloroform and 420 ml of water.

526 Ml of 1:1 by volume of 2N ammonium carbonate and 0.5N sodium carbonate was added. The mixture was quickly filtered and 526 ml of chloroform added to the filtrate. The chloroform was evaporated to about 200 ml and 5 liters of cold acetone were added.

The mixture was filtered through a Buchner funnel, and the recovered DMPG washed with cold acetone.

95 Grams (95% yield) of sodium/ammonium dimyristoylphosphatidyl glycerol was obtained.

The above product was purified further by dissolving in 20% methanol in chloroform, loaded onto a 1 inch silica column and eluted with a mixed solvent of 80% chloroform/20% methanol containing 1% of ammonium hydroxide.

The fraction containing the dimyristoylphosphatidyl glycerol product was separated and evaporated to dryness. Dimyristoylphosphatidyl glycerol mixed ammonium/sodium salt of 99% purity was obtained.

EXAMPLE 3

200 Grams (0.29 mol) of dimyristoylphosphatidyl choline was charged to a five liter three necked flask equipped with a banana paddle to which 1 liter of 0.5N sodium acetate buffer having a pH of 5.6, 1 liter of water, 200 ml of glycerol and 200 ml of M calcium chloride were added. The pH was adjusted to 5.5.

80 Milligrams of phospholipase D dissolved in 5 ml of sodium acetate buffer and 5 ml of water was added to the flask. Finally, 1 liter of methylene chloride was added to the mixture stirred for 17 hours.

The reaction mixture was filtered on a Buchner funnel and the filter cake washed with 5 liters of water and 5 liters of methylene chloride.

166 Grams (0.24 mol) of calcium dimyristoylphosphatidyl glycerol or a yield of 82% was obtained. The product was determined to be 95% pure by thin layer chromatography.

EXAMPLE 4

A series of sample tubes were each charged with a suspension consisting of 200 milligrams of dimyristoylphosphatidyl choline; 2 ml of 0.25M sodium acetate buffer having a pH of 5.6; 200 ml of molar calcium chloride; 200 ml of glycerol and 5 milligrams of phospholipase D in 2 ml of 0.25M sodium acetate buffer having a pH of 5.6.

2.5 ml each of various solvents (see Table I) was added to each tube. The tubes were capped and placed on a shaker at 25° C. The shaker was set at 250 rpm and run for 17 hours. The shaker was stopped and each tube was examined and the contents washed 3 times with 5 ml of chloroform, and then with 5 ml of acetone, and dried in vacuo to a constant weight. A sample of each was analyzed by thin layer chromatography (TLC) on silica gel with chloroform:methanol:ammonia in the volume ratio of 65:35:5. The results are given in Table I below:

TABLE I

| Solvent | Yield of Insoluble Product mg** |
| --- | --- |
| ethyl acetate | 183 |
| ethyl propionate | 205* |
| ethyl butyrate | 254* |
| 2-butanone | 78 |
| 2-pentanone | 78 |
| 2-heptanone | 162 |

TABLE I-continued

| Solvent | Yield of Insoluble Product mg** |
| --- | --- |
| 2-octanone | 166 |
| butyl acetate | 126 |
| 3-pentanone | 150 |
| 3-heptanone | 116 |
| 3-octanone | 9 |
| 4-heptanone | 175 |
| carbon tetrachloride | 5 |
| chloroform | 46 |
| methylene chloride | 185 |
| ether | 190 |

*High values probably due to nonhomogeneous liposome suspension
**TLC showed conversion of phosphatidyl choline to calcium salt of phosphatidyl glycerol with the unreacted phosphatidyl choline being washed away.

EXAMPLES 5-10

The solubility in methylene chloride of various mixed ammonium/sodium salts of dimyristoylphosphatidyl glycerol was determined. 1.6 Mg of each mixed salt was mixed and heated at 35° C. while stirring, for one and two hours. The mixture was filtered through a 0.2 micron 25 mm syringe filter (Gelman Acrodisc CR) and percent solubility was determined. The results are summarized below in Table II.

TABLE II

| Example | % NH$_4$ | % Na+ | % Ca$^{2+}$ | Percent Solubility 1 Hour | Percent Solubility 2 Hours |
| --- | --- | --- | --- | --- | --- |
| 5 | 2.28 | 0.34 | 0.19 | 94 | 98 |
| 6 | 1.64 | 1.11 | 0.06 | 62 | 64 |
| 7 | 1.59 | 1.08 | 0.09 | 60 | 65 |
| 8 | 1.97 | 0.75 | 0.05 | 76 | 83 |
| 9 | 2.32 | 0.55 | 0.33 | — | 92 |
| 10 | 2.11 | 0.51 | 0.26 | — | 79 |

FIG. 1 is a graph of solubility versus ammonium ion content in methylene chloride. The graph shows that even when the calcium exceeds about 0.05% by weight and the sodium content exceeds about 0.8% by weight, the solubility increases markedly when the ammonium ion content is above about 2.0 percent, and is very high when the ammonium ion content is about 2.25 to about 2.35 percent.

EXAMPLE 11

0.2M sodium acetate buffer pH 5.6, is loaded with 0.3M calcium chloride, 0.3M glycerol and phospholipase D into a Centrifugal Partition Chromotography (CPC) system. The centrifuge is set in motion and ethyl acetate or ethyl butyrate containing 0-20% phosphatidyl choline is pumped into the CPC system. The calcium salt of DMPG precipitates from the eluant and may be further purified. The unreacted soluble phosphatidyl choline's may be recirculated.

COMPARATIVE EXAMPLES 1-4

The solubility in methylene chloride of various mixed ammonium/sodium salts of dimyristoylphosphatidyl glycerol was determined. 1.6 Mg of each mixed salt was combined with 4.5 mg of dimyristoylphosphatidyl choline and mixed and heated at 35° C. for one hour. The material was then passed through a 0.2 micron 25 mm syringe filter (Gelman Acrodisc CR) and the percent of insolubles was calculated. The results are summarized below in Table III.

TABLE III

| Example | Percent by weight | | | Solubles % | Percent Insolubles |
|---|---|---|---|---|---|
| | Na+ | NH4+ | Ca2+ | | |
| C1 | 0.38 | 2.26 | 0.2 | 95 | 5 |
| C2 | 0.51 | 2.11 | 0.26 | 89 | 11 |
| C3 | 1.11 | 1.64 | 0.06 | 91 | 9 |
| C4 | 0.75 | 1.97 | 0.05 | 95 | 5 |

COMPARATIVE EXAMPLE 5

A batch of 1.6 mg/ml of mixed ammonium/sodium dimyristoylphosphatidyl glycerol having a sodium content of 1.20%, ammonium content of 1.53% and calcium content of 0.12% by weight of the salt, was admixed with 4.5 mg/ml of dimyristoylphosphatidyl choline in methylene chloride, and heated at 35° C. while stirring. The mixture was still cloudy after one hour, indicating incomplete solubilization of the mixed salt.

What is claimed is:

1. A process for forming a soluble monovalent salt of a phosphatidyl ester which comprises:
    a) reacting a phospholipid with a primary alcohol in the presence of
        (i) phospholipase D,
        (ii) a divalent cationic buffer solution, and
        (iii) a water immiscible non-ether solvent so as to form the corresponding phosphatide of the divalent cationic salt; and
    b) converting the divalent cationic salt to an organic soluble monovalent salt by suspending with a stoichiometric amount of a monovalent salt having a monovalent cation and whose anion forms an insoluble precipitate with the divalent cation.

2. The process according to claim 1 wherein the phospholipid is phosphatidyl choline.

3. The process according to claim 1 wherein the phospholipid is dimyristoylphosphatidyl choline.

4. The process according to claim 1 wherein the alcohol is selected from the group consisting of glycerol, sulfocholine, ethylene glycol, glycidol, ribose, ethanolamine, glycerolformal and sialic acids.

5. The process according to claim 4 wherein the alcohol is glycerol.

6. The process according to claim 1 wherein the buffer solution contains a calcium salt.

7. The process according to claim 1 wherein the water immiscible solvent is a halogenated alkane or alkene selected from the group consisting of methylene chloride, chloroform, tetrachloroethylene and trichlorofluoromethane.

8. The process according to claim 1 wherein the water immiscible solvent is an aliphatic or aromatic ester, alkane, ketone.

9. The process according to claim 8 wherein the water immiscible solvent is a member of the group consisting of ethyl acetate, ethyl propionate, ethyl butyrate, methyl acetate, methyl propionate, 2-butanone, 2-pentanone, 2-heptanone, 2-octanone, 3-pentanone, 3-heptanone, 3-octanone and 4-heptanone.

10. The process according to claim 1 wherein the monovalent cation of the monovalent salt is selected from one or more of the group consisting of ammonium, sodium and potassium.

11. The process according to claim 10 wherein the anion of the salt is a carbonate, citrate, sulfate, phosphate, nitrate, lactate, succinate, formate, oxalate, ethylene tetraacetate, ethylene bis(oxyethylene nitrilo)tetraacetate, or chloride.

12. The process according to claim 1 wherein step a) is carried out using Centrifugal Partition Chromatography.

13. A process for forming a soluble mixed ammonium/sodium salt of dimyristoylphosphatidyl glycerol which comprises:
    a) reacting a dimyristoylphospholipid with a primary alcohol in the presence of
        (i) phospholipase D,
        (ii) a divalent cationic buffer solution, and
        (iii) an aqueous-immiscible non-ether solvent, so as to form the corresponding phosphatide of the divalent cationic salt; and
    b) converting the divalent cationic salt to an organic soluble monovalent salt by suspending with a stoichiometric amount of a monovalent salt whose anion forms a precipitate with the divalent cation and whose cation is a mixture of ammonium and sodium in a weight ratio so as to form a mixed monovalent dimyristoylphosphatidyl glycerol containing from about 2.0 to 2.6% by weight of ammonium and from about 0.3 to 0.8% by weight of sodium.

14. The process according to claim 13 wherein the divalent cation is calcium.

15. The process according to claim 13 wherein the mixed monovalent dimyristoylphosphatidyl glycerol contains not more than about 0.1% by weight of the mixed salt of calcium.

16. The process according to claim 15 wherein the mixed monovalent dimyristoylphosphatidyl glycerol contains not more than about 0.05% by weight of the mixed salt of calcium.

17. The process according to claim 13 wherein step a is carried out using Centrifugal Partition Chromotography.

* * * * *